(12) United States Patent
Armbruster et al.

(10) Patent No.: US 12,121,635 B2
(45) Date of Patent: Oct. 22, 2024

(54) SYSTEMS AND METHODS FOR FORMING AN ANTIMICROBIAL ORTHOPEDIC IMPLANT

(71) Applicant: DePuy Synthes Products, Inc., Raynham, MA (US)

(72) Inventors: David A. Armbruster, West Chester, PA (US); Charles Florek, Downingtown, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 957 days.

(21) Appl. No.: 17/102,671

(22) Filed: Nov. 24, 2020

(65) Prior Publication Data
US 2021/0154374 A1 May 27, 2021

Related U.S. Application Data

(60) Provisional application No. 62/940,930, filed on Nov. 27, 2019.

(51) Int. Cl.
*A61L 31/16* (2006.01)
*A61B 50/30* (2016.01)
(Continued)

(52) U.S. Cl.
CPC .............. *A61L 31/16* (2013.01); *A61B 50/30* (2016.02); *A61L 31/08* (2013.01);
(Continued)

(58) Field of Classification Search
CPC ................... A61B 50/30; A61B 50/39; A61B 17/80–8095; A61L 2300/202;
(Continued)

(56) References Cited

U.S. PATENT DOCUMENTS 5,538,428 A * 7/1996 Staubli ................. A61C 8/0087
206/63.5
6,047,815 A 4/2000 Cerwin et al.
(Continued)

FOREIGN PATENT DOCUMENTS

CN 1713854 A 12/2005
CN 102599953 A 7/2012
(Continued)

OTHER PUBLICATIONS

Eman S. Zarie et al: Solvent Free Fabrication of Micro and Nanostructured Drug Coatings by Thermal Evaporation for Controlled Release and Increased Effects, PLOS ONE, vol. 7, No. 8, Aug. 1, 2012 (Aug. 1, 2012), p. e40746, XP055545130.

*Primary Examiner* — Matthew J Lawson
(74) *Attorney, Agent, or Firm* — BakerHostetler

(57) ABSTRACT

Systems, methods of manufacture, and packaging configurations are provided for an antimicrobial orthopedic implant having an antimicrobial coating on the outer surface of the implant including a vaporizable antimicrobial agent in a surface area concentration on the outer surface sufficient to prevent bacterial growth on the orthopedic implant, and can additionally provide a clinically effective zone of inhibition around the orthopedic implant. In certain embodiments, a container, a reservoir of the vaporizable antimicrobial agent, and the orthopedic implant are configured to remain thermally stable in a temperature range up to 200 C.

18 Claims, 5 Drawing Sheets

(51) Int. Cl.
 *A61L 31/08* (2006.01)
 *B05D 1/00* (2006.01)

(52) U.S. Cl.
 CPC ... *A61L 2300/202* (2013.01); *A61L 2300/404* (2013.01); *A61L 2420/02* (2013.01); *B05D 1/60* (2013.01)

(58) Field of Classification Search
 CPC ..... A61L 2420/02; A61C 8/0016; A61C 8/00; A61C 8/0012
 USPC .................................................. 606/301–321
 See application file for complete search history.

(56) References Cited

U.S. PATENT DOCUMENTS

| | | | |
|---|---|---|---|
| 6,135,272 A | 10/2000 | Sobel et al. | |
| 6,915,623 B2 | 7/2005 | Dey et al. | |
| 7,513,093 B2 | 4/2009 | Scalzo et al. | |
| 8,112,973 B2 | 2/2012 | Fischer et al. | |
| 8,133,437 B2 | 3/2012 | Scalzo et al. | |
| 8,156,718 B2 | 4/2012 | Scalzo et al. | |
| 8,668,867 B2 | 3/2014 | Scalzo et al. | |
| 8,960,422 B2 | 2/2015 | Cerwin et al. | |
| 9,044,531 B2 | 6/2015 | Dave et al. | |
| 9,149,273 B2 | 10/2015 | Fischer et al. | |
| 9,474,524 B2 | 10/2016 | Fischer et al. | |
| 9,597,067 B2 | 3/2017 | Reyhan et al. | |
| 9,597,072 B2 | 3/2017 | Fischer et al. | |
| 2004/0068293 A1 | 4/2004 | Scalzo et al. | |
| 2005/0173270 A1* | 8/2005 | Bourne | B65D 25/08 206/219 |
| 2006/0091035 A1* | 5/2006 | Scalzo | A61B 17/06166 206/439 |
| 2007/0170080 A1* | 7/2007 | Stopek | A61B 50/30 206/438 |
| 2010/0082064 A1* | 4/2010 | Chun | A61L 27/04 606/246 |
| 2010/0268282 A1* | 10/2010 | Trieu | A61B 17/8042 606/280 |
| 2012/0215307 A1* | 8/2012 | Chen | A61F 2/186 623/10 |
| 2012/0267263 A1* | 10/2012 | Fischer | A61L 17/005 53/425 |
| 2013/0216599 A1 | 8/2013 | Kumar et al. | |
| 2014/0174971 A1* | 6/2014 | Lindner | A61B 50/30 53/426 |
| 2020/0030065 A1* | 1/2020 | Touati | A61C 9/0046 |

FOREIGN PATENT DOCUMENTS

| | | |
|---|---|---|
| WO | 2004/032703 A2 | 4/2004 |
| WO | 2011/098565 A1 | 8/2011 |
| WO | 2015/013629 A1 | 1/2015 |

\* cited by examiner

SYSTEMS AND METHODS FOR FORMING AN ANTIMICROBIAL ORTHOPEDIC IMPLANT

CROSS REFERENCE TO RELATED APPLICATIONS

This application claims the benefit of U.S. Provisional Application No. 62/940,930, filed on Nov. 27, 2019, the contents of which are hereby incorporated by reference in their entirety.

FIELD OF DISCLOSURE

The present disclosure is directed to systems, method of manufacture, and packaging configurations for an antimicrobial orthopedic implant having an antimicrobial coating on the outer surface of the implant including a vaporizable antimicrobial agent in a surface area concentration on the outer surface sufficient to prevent bacterial growth on the orthopedic implant, and can additionally provide a clinically effective zone of inhibition around the orthopedic implant.

BACKGROUND

Many individuals receive orthopedic surgical implants every year as a result of orthopedic trauma or joint replacement procedures. In the United States over 600,000 artificial knee prostheses and over 300,000 artificial hip prostheses are implanted every year according to the American Academy of Orthopedic Surgeons. More than one million patients each year receive metal implants for treatment of broken bones. Implant related infection is one of the most severe potential complications related to orthopedic implants, with infection rates of over 10% in some high-risk procedures and patient groups. The cost of treating implant related infection is significant, because treatment often requires surgical removal of the infected implant and extended treatment with antibiotics.

Implant related infections are caused when bacteria contaminate a surgical wound site, attach to the surgical implant, and begin to proliferate. Bacteria growing on an implant surface often form a biofilm, in which they secrete a protective extracellular matrix and their metabolic activity is significantly reduced. This biofilm phenotype protects the bacteria from the patient's immune system and from systemic antibiotics, which makes treatment of implant related infection very difficult and costly.

One solution to preventing implant related infection is to treat the surface of the surgical implant in a way that prevents bacterial growth and attachment. Surgical implants have been developed that are coated with antibiotics or antimicrobial compounds to kill bacteria in the surgical wound site or on the implant surface before they can attach and proliferate on the implant. Examples include antimicrobial coated pacemaker pouches (TYRX™ Absorbable Antimicrobial Envelope), orthopedic implants (ETN PROtect), surgical graft materials (XenMatrix™ AB Surgical Graft), and sutures (VICRYL® Plus Antimicrobial Suture).

Methods have been disclosed for vapor transfer of a vaporizable antimicrobial agent to a medical device such as a suture by placing the device in an inner package having a source of antimicrobial agent, covering the inner package with an outer package, and subjecting the device and package to time, temperature and pressure conditions sufficient to vapor transfer the antimicrobial agent from the antimicrobial agent source to the device (e.g., U.S. Pat. Nos. 7,513,093; 8,112,973; 8,133,437; 8,156,718; 8,668,867; 8,960,422; 9,044,531; 9,149,273; 9,474,524; 9,597,067; 9,597,072). This vapor transfer process has demonstrated success in transferring an antimicrobial agent to polymer or paper materials (such as surgical sutures or packaging materials).

SUMMARY

The present inventors have surprisingly discovered that the processes previously described in the art for vapor deposition of an antimicrobial agent (typically, materials and conditions directed to standard ethylene oxide sterilization parameters) do not provide a clinically effective coating on all orthopedic implant materials. For example, orthopedic implants having a metal substrate surface do not retain an amount of the antimicrobial agent sufficient to inhibit bacterial growth. Further, the distribution of the antimicrobial agent along the surface of the orthopedic implant can be non-uniform. This can be the result of the ethylene oxide sterilization parameters which utilize a packaging configuration that have vents that allow for vapor transfer from the environment into the package to allow for the infiltration of ethylene oxide gas, but likewise permits the escape of large quantities of volatilized antimicrobial agent to the external environment. Additionally, ethylene oxide sterilization typically involves a vacuum phase which pulls additional vaporized antimicrobial agent from the package. Finally, certain packaging materials used in ethylene oxide sterilization can have a greater ability to absorb the vaporizable antimicrobial agent than a metal substrate, such as for example, certain biocompatible polymers used in packaging as well as used as implantable medical devices (e.g., sutures) and certain medical grade paper.

Accordingly, the present disclosure is directed to systems and methods for providing an antimicrobial coating on the outer surface of an orthopedic implant (preferably an implant with at least a partially metal or metal alloy outer surface) where the antimicrobial coating contains a vaporizable antimicrobial agent in a surface area concentration sufficient inhibit bacterial growth on the implant surface, and additionally, in certain embodiments, provide a clinically effective zone of inhibition around the implant.

According to the present disclosure, methods of forming an antimicrobial orthopedic implant are disclosed, the methods including:
  providing a container having a first end and a second end, and an inner surface extending between the first and seconds ends, the inner surface defining a container cavity, where the first end defines an opening extending into the container cavity;
  placing a reservoir of a vaporizable antimicrobial agent in the container cavity, wherein the inner surface comprises a material that is non-absorbent to the vaporizable antimicrobial agent;
  placing an orthopedic implant in the container cavity through the first end, the orthopedic implant defining an outer surface;
  sealing the first end of the container so as to seal the container cavity;
  heating the container while sealed so as to heat the outer surface of the orthopedic implant and the reservoir of vaporizable antimicrobial agent so as to cause a vaporization of the antimicrobial agent; and,
  cooling the container while sealed;
  where the heating and cooling of the container causes the vaporized antimicrobial agent to adsorb on the outer surface of the orthopedic implant such that an antimicrobial coated orthopedic implant is formed having a surface area concentration of antimicrobial agent on the outer surface of the orthopedic implant that is sufficient to produce a clinically effective zone of inhibition of at least 0.5 mm from a periphery of the outer surface. In preferred embodiments, the surface area concentration is sufficient to prevent bacterial colonization on the outer surface of orthopedic implant. In certain other embodiments, the surface area concentration of the orthopedic implant is equal to or greater than a surface area concentration of the antimicrobial agent on the inner surface of the container.

According to further embodiments the methods can include depositing a solution of the vaporizable antimicrobial agent and a solvent into the cavity and evaporating the solvent from the cavity and out of the container. In alternative embodiments, the methods can include coating a solution of the vaporizable antimicrobial agent and a solvent onto the inner surface of the container and evaporating the solvent from the inner surface and out of the container.

In additional embodiments, the step of heating includes heating to a temperature range of about 60 C to about 200 C, for example in the range of about 80 C to about 180 C, about 100 C to 170 C, or about 120 C to about 160 C. In still additional embodiments, the step of heating is in the range of about 10 min to about 8 hours, for example from about 3 hours to about 6 hours.

According to certain embodiments, the container is substantially rigid such that the cavity defines a fixed volume.

According to certain embodiments, the container first end includes a threaded region extending around an outer surface of the container, where the threaded region is configured to engage with a lid having a corresponding threaded region on an inner surface such that the step of sealing the first end of the container includes engaging the first end threaded region and the lid threaded region. Embodiments can additionally include a seal member configured to be disposed between and in contact with the lid threaded region and the first end threaded region during the step of sealing.

According to alternative embodiments, the container is substantially deformable, and the cavity defines a first geometry having a first volume when the first end is open such that upon deformation the cavity assumes a second geometry having a second volume smaller than the first volume. In certain other embodiments, the first end is substantially deformable, and the step of sealing includes applying pressure to the first end so as to force opposing walls of the inner surface at the first end to contact one another and seal the first end. In additional embodiments, at least a portion of the inner surface at the first end includes an amount of sealing agent such that the upon contact the opposing walls are bonded to one another so as to seal the first end. In additional alternative embodiments, the step of sealing can include applying a mechanical fastener to the sealed first end configured to keep the opposing walls in contact with one another.

In still further embodiments of the container, the second end is open, and the step of sealing the container further includes sealing the second end. In certain embodiments, the second end is substantially deformable, such that the step of sealing further includes applying pressure to the second end so as to force opposing walls of the inner surface at the second end to contact one another and seal the second end.

According to the present disclosure the antimicrobial coated orthopedic implant includes an antimicrobial coating on the outer surface where the surface area concentration of the antimicrobial agent on the outer surface of the orthopedic implant in the range of about 5 µg/cm$^2$ to about 1000 µg/cm$^2$, for example in the range of about 10 µg/cm$^2$ to about 1000 µg/cm$^2$. In additional embodiments, the antimicrobial agent in the reservoir has a total weight and the vapor deposition causes at least 1% to about 95% of the total weight, for example about 1% to 10%, or about 10% to about 20%, of the antimicrobial agent to form the antimicrobial coating on the outer surface of the orthopedic implant.

According to the present disclosure, a system for forming an antimicrobial orthopedic implant as described in the process above includes:

a reservoir of a vaporizable antimicrobial agent;

an orthopedic implant defining an outer surface; and, a container having a first end and a second end, and an inner surface extending between the first and second ends, the inner surface defining a cavity configured to receive the orthopedic implant, where the first end defines a sealable opening extending into the cavity;

wherein the inner surface comprises a material that is non-absorbent to the vaporizable antimicrobial agent;

where the container, the orthopedic implant, and the vaporizable antimicrobial agent are configured to remain thermally stable in a temperature range up to 200 C;

where the reservoir of vaporizable antimicrobial agent is disposed in the container;

where the orthopedic implant is disposed within the cavity, and where the outer surface is substantially free of the vaporizable antimicrobial agent.

According to certain embodiments, at least a portion of the inner surface at the first end includes an amount of sealing agent configured to bond the opposing walls to one another so as to seal the first end where the sealing agent includes, for example, an adhesive material or a thermal bonding material.

According to the present disclosure a packaging configuration for a sterile antimicrobial orthopedic implant is described including:

a sterile container having a first end and a second end, and an inner surface extending between the first and second ends, the inner surface defining a cavity, where the first end defines a sealable opening extending into the cavity;

a sterile orthopedic implant disposed in the cavity, the orthopedic implant defining an outer surface;

where the orthopedic implant has an antimicrobial coating on the outer surface, the antimicrobial coating including a surface area concentration of a vaporizable antimicrobial agent on the outer surface of the orthopedic implant;

wherein the inner surface comprises a material that is non-absorbent to the vaporizable antimicrobial agent and, where the outer surface has a surface area concentration of the vaporizable antimicrobial agent in the range of about 5 µg/cm$^2$ to about 1000 µg/cm$^2$.

According to certain embodiments, the vaporizable antimicrobial agent has a total weight, and at least 1% to about 20% of the total weight of the vaporizable antimicrobial agent is contained in the antimicrobial coating on the orthopedic implant.

According to the present disclosure, an antimicrobial coated implant is described including:

an orthopedic implant, the orthopedic implant defining an outer surface consisting essentially of a metal or metal alloy, a polyalkene or copolymer thereof, or a polyaryletherketone or copolymer thereof, or a combination thereof; and, an antimicrobial coating disposed on the outer surface of the orthopedic implant, the antimicrobial implant consisting essentially of a vaporizable antimicrobial agent; and, where the antimicrobial coated implant has a surface area concentration of antimicrobial agent on the outer surface of the orthopedic implant in the range of about 5 µg/cm$^2$ to about 1000 µg/cm$^2$. In a preferred embodiment, the surface area concentration is effective to prevent microbial colonization of the orthopedic implant. In certain additional embodiments, the surface area concentration is effective to produce a zone of inhibition against microbial colony forming units of at least 0.5 mm from the outer surface of the orthopedic implant.

According to certain embodiments, the vaporizable antimicrobial agent includes halogenated hydroxyl ethers, acyloxydiphenyl ethers, or combinations thereof. In a preferred embodiment, the vaporizable antimicrobial agent includes 2,4,4'-trichloro-2'-hydroxydiphenyl ether (triclosan).

In certain embodiments, the outer surface of the orthopedic implant includes at least a polyaryletherketone (PAEK) or a polyalkene or copolymer thereof, or a metal or metal alloy, or a combination thereof. In preferred embodiments, the outer surface is titanium or stainless steel, or alloys thereof; or a polyethylene or polyetheretherketone (PEEK) or a copolymer thereof.

In other embodiments, the inner surface of the container includes a material that is non-absorbent to the vaporizable antimicrobial agent, such as a metal or a metal alloy, for example aluminum or an alloy thereof. In certain embodiments, the metal or metal alloy is the form of micronized or sub-micronized metal particles applied to the inner surface of the container.

According to certain embodiments, the outer surface consists essentially of a metal or metal alloy, and a polyalkene or copolymer thereof, for example titanium or stainless steel or alloys thereof, and polyethylene or copolymers thereof. According to certain embodiments, the outer surface consists essentially of a metal or metal alloy, and a polyaryletherketone or copolymer thereof, for example titanium or stainless steel or alloys thereof, and PEEK or copolymers thereof. According to certain embodiments, the outer surface consists essentially of polyalkene or copolymer thereof, and a polyaryletherketone or copolymer thereof, for example, polyethylene or copolymer thereof, and PEEK or copolymer thereof.

According to certain embodiments, the surface area concentration of the antimicrobial agent in the antimicrobial coating is in the range of about 10 µg/cm$^2$ to about 1000 µg/cm$^2$.

According to certain embodiments, the ZOI is in the range of about 0.5 mm to about 5.0 mm.

BRIEF DESCRIPTION OF THE DRAWINGS

The drawings illustrate generally, by way of example, but not by way of limitation, various embodiments discussed in the present disclosure. The foregoing summary, as well as the following detailed description of preferred embodiments of the application, will be better understood when read in conjunction with the appended drawings.

DETAILED DESCRIPTION

Figure 1A:
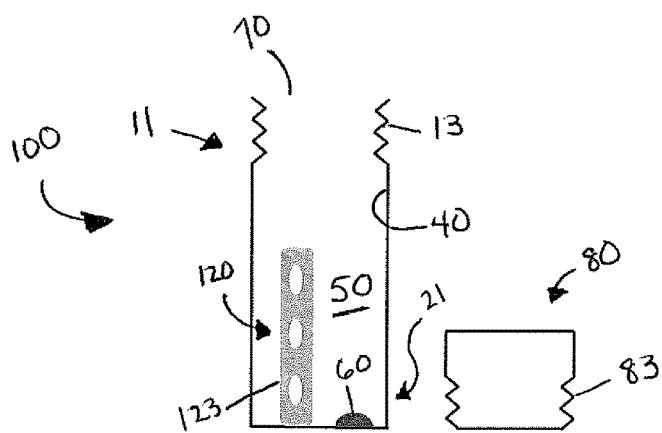
FIGS. 1A-C are a schematic representation of a packaging system and process of forming antimicrobial coating on an orthopedic implant according to embodiments of the present disclosure.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable. Further, reference to values stated in ranges includes each and every value within that range. It is also to be appreciated that certain features of the invention, which, for clarity, are described herein in the context of separate embodiments, may also be provided in combination in a single embodiment. Conversely, various features of the invention that are, for brevity, described in the context of a single embodiment, may also be provided separately or in any subcombination.

As used herein the term "absorb" refers to the process of a chemical in a vapor or liquid form penetrating into the surface of a solid material, to be present at some depth beneath the surface. The term "absorbent" refers to the tendency of a solid material to absorb a chemical from the liquid or vapor phase. The term "nonabsorbent" is used to describe a material that does not have a tendency to absorb a chemical liquid or vapor, or absorbs a liquid or vapor in very low quantities.

As used herein the term "adsorb" refers to the process of a chemical in a vapor or liquid form forming a thin layer on the surface of a solid material.

As used herein the phrase "consisting essentially of" is intended to define the scope of a claim as including the recited materials or steps and additionally include any materials and steps that do not materially affect the basic characteristics of the claimed invention.

The present disclosure is directed to the previously undiscovered problem that vapor deposition of triclosan under conditions approximating standard ethylene oxide (EO) sterilization, in certain circumstances, does not provide uniform and clinically effective coatings on certain implantable medical device surfaces. One particular set of implants is orthopedic implants having metal or metal alloy substrate surfaces. These types of implants when processed under EO sterilization conditions with a triclosan reservoir do not produce a zone of inhibition sufficient to inhibit bacterial growth. When following the described EO sterilization processes described in the prior art, only a small fraction of the triclosan in the package is transferred to the implant surface. A significant portion of the triclosan dose is lost from the package container during the vacuum phase of the ethylene oxide sterilization process. Another significant portion of the triclosan dose is absorbed by the packaging components such as the polymer and paper components of the packaging. Because of these losses, the EO triclosan transfer process is inefficient in its yield of triclosan on the finished product, and the dosing of the final product is variable.

Accordingly, the present disclosure is directed to systems and methods for producing antimicrobial coatings on orthopedic implant surfaces using vapor deposition of an antimicrobial agent that provides a clinically effective zone of inhibition at an implant site, and can simultaneously provide regulatory approved sterilization to the implant and its attendant packaging components. Importantly, the removal of packaging components that have an affinity for triclosan absorption is a desired result. Additionally, the ability to accurately and uniformly dose the outer surface of an implant is a desired result. One advantage of using a metal sterilization container is its higher thermal stability relative to common polymer packaging materials for medical devices. Because triclosan is also thermally stable at temperatures up to and above 160° C., the triclosan vapor transfer conditions may also function as conditions for dry heat sterilization of the implant. This allows the triclosan vapor to be accomplished by the same process and at the same time as terminal sterilization of the implant.

More specifically, an additional benefit of the present disclosure is the ability to use the described antimicrobial vapor transfer processes during what is known as "dry heat" (or also "high heat") sterilization processes as opposed to current state of the art processes relying on EO sterilization parameters. Ethylene oxide is poisonous, highly flammable, toxic, and a known carcinogen. In the United States, the operation of EO sterilization is overseen by the EPA through the National Emission Standard for Hazardous Air Pollutants. One advantage of using a sterilization container having a thermally stable inner surface that is non-absorbent to the vaporizable antimicrobial agent, such as a metal inner surface, is its higher thermal stability relative to common polymer packaging materials for medical devices. Because triclosan is also thermally stable at temperatures up to and above 160° C., the triclosan vapor transfer conditions may also function as conditions for dry heat sterilization of the implant. This allows the triclosan vapor transfer process to be accomplished by the same process and at the same time as "dry heat" terminal sterilization of the implant. As such, the ability to provide an alternate for implantable medical device sterilization process that can replace current EO sterilization processes and still provide clinically effective antimicrobial coatings is desirable, and a valuable benefit in the orthopedic implant industry.

As used herein "zone of inhibition" (ZOI) means the distance measured from the periphery of an implant where there is no measurable microbial colony forming units (e.g., microbial activity), when the implant is placed in an in vitro environment inoculated with a known quantity of colony forming microorganisms. In certain literature, ZOIs are measured as the entire cross-sectional length of an area (e.g., a diameter) where no measurable microbial activity is present and can include the implant's dimensions as well.

As used herein "clinically effective zone of inhibition" means a ZOI measurement of at least 0.5 mm around the perimeter of an implant that is free of measurable bacterial growth.

As used herein "vaporizable" means an antimicrobial compound that can evaporate when exposed to temperatures above 50 C at ambient pressure conditions.

According to the present disclosure, methods of forming an antimicrobial orthopedic implant are disclosed, the methods including:
  providing a container having a first end and a second end, and an inner surface extending between the first and seconds ends, the inner surface defining a container cavity, wherein the first end defines an opening extending into the container cavity;
  placing a reservoir of a vaporizable antimicrobial agent in the container cavity, wherein the inner surface comprises a material that is non-absorbent to the vaporizable antimicrobial agent;
  placing an orthopedic implant in the container cavity through the first end, the orthopedic implant defining an outer surface;
  sealing the first end of the container so as to seal the container cavity;
  heating the container while sealed so as to heat the outer surface of the orthopedic implant and the reservoir of vaporizable antimicrobial agent so as to cause a vaporization of the antimicrobial agent; and,
  cooling the container while sealed;
  where the heating and cooling of the container causes the vaporized antimicrobial agent to adsorb on the outer surface of the orthopedic implant such that an antimicrobial coated orthopedic implant is formed having a surface area concentration of antimicrobial agent on the outer surface of the orthopedic implant that is sufficient to produce a clinically effective zone of inhibition of at least 0.5 mm from a periphery of the outer surface. In certain embodiments, the surface area concentration of the orthopedic implant is equal to or greater than a surface area concentration of the antimicrobial agent on the inner surface of the container.

According to the present disclosure, a system for forming an antimicrobial orthopedic implant as described in the process above includes:
  a reservoir of a vaporizable antimicrobial agent;
  an orthopedic implant defining an outer surface; and,
  a container having a first end and a second end, and an inner surface extending between the first and second ends, the inner surface defining a cavity configured to receive the orthopedic implant, where the first end defines a sealable opening extending into the cavity; wherein the inner surface comprises a material that is non-absorbent to the vaporizable antimicrobial agent;
  where the container, the orthopedic implant, and the vaporizable antimicrobial agent are configured to remain thermally stable in a temperature range up to 200 C;
  where the reservoir of vaporizable antimicrobial agent is disposed in the container;
  where the orthopedic implant is disposed within the cavity, and where the outer surface is substantially free of the vaporizable antimicrobial agent.

According to the present disclosure a packaging configuration for a sterile antimicrobial orthopedic implant is described including:
  a sterile container having a first end and a second end, and an inner surface extending between the first and second ends, the inner surface defining a cavity, where the first end defines a sealable opening extending into the cavity;

a sterile orthopedic implant disposed in the cavity, the orthopedic implant defining an outer surface;

where the orthopedic implant has an antimicrobial coating on the outer surface, the antimicrobial coating including a surface area concentration of a vaporizable antimicrobial agent on the outer surface of the orthopedic implant;

wherein the inner surface comprises a material that is non-absorbent to the vaporizable antimicrobial agent;

where the inner surface has a surface area concentration of the vaporizable antimicrobial agent; and, where the surface area concentration of the antimicrobial coating on the orthopedic implant is in the range of about 5 μg/cm² to about 1000 μg/cm².

According to the present disclosure, an antimicrobial coated implant is described including:

an orthopedic implant, the orthopedic implant defining an outer surface consisting essentially of a metal or metal alloy, a polyalkene or copolymer thereof, or a polyaryletherketone or copolymer thereof, or a combination thereof; and, an antimicrobial coating disposed on the outer surface of the orthopedic implant, the antimicrobial implant consisting essentially of a vaporizable antimicrobial agent; and, where the antimicrobial coated implant has a surface area concentration of antimicrobial agent on the outer surface of the orthopedic implant in the range of about 5 μg/cm² to about 1000 μg/cm². In certain embodiments, the surface area concentration is effective to produce a zone of inhibition against microbial colony forming units of at least 0.5 mm from the outer surface of the orthopedic implant. In certain further embodiments, the surface area concentration is effective in preventing microbial colonization of the outer surface of the orthopedic implant.

Figure 1B:
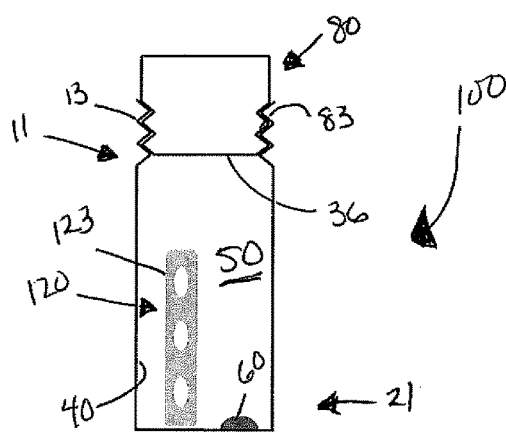
Figure 1C:
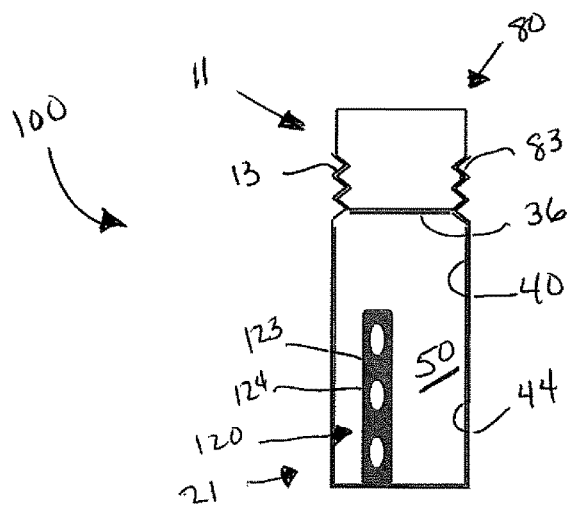

With reference to FIGS. 1A-C, a method of forming of forming an antimicrobial orthopedic implant is disclosed. The method includes providing a container 100 having a first end 11 and second end 21, and an inner surface 40 extending between the first 11 and second 21 ends. The inner surface can define a container cavity 50, and the first end 11 can define an opening 70 extending through the container 100 into the cavity 50. According to embodiments of the present invention the inner surface includes a material that is non-absorbent to the vaporizable antimicrobial agent.

The method further includes the step of placing a reservoir 60 of a vaporizable antimicrobial agent in the container cavity 50. The method additionally includes the step of placing an orthopedic implant 120 in the cavity 50 through the first end 11, where the orthopedic implant 120 defines an outer surface 123.

Container Inner Surface

As described the inner surface 40 includes a non-absorbent material. Non-absorbent material as used herein, is defined relative to the described vaporizable anti-microbial agent, such that the material comprising the inner surface 40 is resistant to the absorption of the antimicrobial agent. The vaporizable antimicrobial agent, however, may adsorb on the inner surface 40. Suitable non-absorbent materials will include most metal and metal alloys. Preferred non-absorbent materials include aluminum and alloys thereof, and stainless steel. Additionally, materials that otherwise would be absorbent to vaporizable antimicrobial agents can be rendered non-absorbent at least along the inner surface 40 of the container 100. For example, with reference to FIGS. 4A-B, an inner surface 40 is shown at a first end 11 having a sealing agent 35 in the form of a thermal bonding layer. As shown, layer 35 has been metalized at the inner surface 40 with submicron size metal particles 32. The particles 32 render the inner surface 40 non-absorbent, but do not substantially interfere with the function of the thermal bonding layer 35 to seal the first end 11.

Vaporizable Antimicrobial Agent

Suitable antimicrobial agents may be selected from, but are not limited to, halogenated hydroxyl ethers, acyloxydiphenyl ethers, or combinations thereof. In particular, the antimicrobial agent may be a halogenated 2-hydroxydiphenyl ether and/or a halogenated 2-acyloxy diphenyl ether, for example, as represented by the following formula:

$$\left[ \underset{3'\ \ 2'}{\underset{4'}{\overset{5'\ \ 6'}{\bigcirc}}} A - O - \underset{2\ \ 3}{\underset{ZO}{\overset{6\ \ 5}{\bigcirc}}} B \right]_4 -(Hal)_w$$

In the above formula, each Hal represents identical or different halogen atoms, Z represents hydrogen or an acyl group, and w represents a positive whole number ranging from 1 to 5, and each of the benzene rings, but preferably ring A can also contain one or several lower alkyl groups which may be halogenated, a lower alkoxy group, the allyl group, the cyano group, the amino group, or lower alkanoyl group. Preferably, methyl or methoxy groups are among the useful lower alkyl and lower alkoxy groups, respectively, as substituents in the benzene rings. A halogenated lower alkyl group, trifluoromethyl group is preferred.

Antimicrobial activity similar to that of the halogen-o-hydroxy-diphenyl ethers of the above formula is also attained using the O-acyl derivatives thereof which partially or completely hydrolyze under the conditions for use in practice. The esters of acetic acid, chloroacetic acid, methyl or dimethyl carbamic acid, benzoic acid, chlorobenzoic acid, methylsulfonic acid and chloromethylsulfonic acid are particularly suitable.

One particularly preferred antimicrobial agent within the scope of the above formula is 2,4,4'-trichloro-2'-hydroxydiphenyl ether, commonly referred to as triclosan. Triclosan is a broad-spectrum antimicrobial agent that has been used in a variety of products and is effective against a number of organisms commonly associated with SSIs. Such microorganisms include, but are not limited to, genus *Staphylococcus, Staphylococcus epidermidis, Staphylococcus aureus*, methicillin-resistant *Staphylococcus epidermidis*, methicillin-resistant *Staphylococcus aureus*, and combinations thereof.

According to further embodiments the methods can include depositing a solution of the vaporizable antimicrobial agent and a solvent into the cavity 50 and evaporating the solvent from the cavity 50 and out of the container 100 so as to form a reservoir 60 of the vaporizable antimicrobial agent in the cavity 50. In alternative embodiments, the methods can include coating a solution of the vaporizable antimicrobial agent and a solvent onto the inner surface 40 of the container 100 and evaporating the solvent from the inner surface 40 and out of the container 100 so as to form a reservoir 60 of vaporizable antimicrobial agent.

Orthopedic Implant

Orthopedic implants are understood to be implantable medical devices that either aid in the repair of damaged bone, or are a prosthesis used for replacing bone. An exemplary, and non-limiting, list of suitable orthopedic implants according to the present disclosure can include bone plates, intramedullary nails, bone screws, pins, spinal rods, K-wires, intervertebral disc replacements, metal compression staples (e.g., Nitinol), metal meshes such as used in craniomaxillofacial applications, external fixation screws or pins (e.g., Schanz screws and Steinmann pins), as well as joint replacement components used in hip, knee, and shoulder replacement procedures, such as, acetabular cups, femoral stems, tibial trays, artificial patella, and femoral condyle components.

As described, the orthopedic implant defines an outer surface 123. The outer surface according to certain preferred embodiments may comprise a metal or metal alloy, a polyaryletherketone (PAEK) or copolymer thereof, or a polyalkene or copolymer thereof; or any combination of the aforementioned materials. Suitable metals can include, for example, titanium, stainless steel, nickel, cobalt, chromium, and metal alloys of the same. A preferred polyalkene is polyethylene or copolymer thereof. Suitable examples include high density polyethylene (HDPE), ultrahigh molecular weight polyethylene (UHMWPE), medium density polyethylene (MDPE), ultra low molecular weight polyethylene (ULMWPE), high molecular weight polyethylene (HMWPE), high density cross-linked polyethylene (HDXLPE), cross-linked polyethylene (PEX or XLPE), linear low density polyethylene (LLDPE), low density polyethylene (LDPE), or very low density polyethylene (VLDPE), as well as blends or copolymers thereof. Under certain elevated temperature conditions as will be further described below, one of skill in the art can determine which polyalkenes or copolymers thereof have the necessary chemical properties to withstand conditions requiring elevated temperatures; e.g., greater than 100 C without suffering thermal degradation or other undesired effects. Suitable examples of PAEK polymers include but are not limited to, polyetheretherketone (PEEK) carbon reinforced PEEK, polyetherketoneketone (PEKK), polyetherketone (PEK), or polyetherketoneetherketoneketone (PEKEKK), or blends or copolymers thereof.

It should be appreciated that in certain embodiments, a thin film of an absorbent biocompatible polymer material can be applied to the outer surface of the orthopedic implant in order to further increase the resultant surface area concentration of the vaporizable antimicrobial agent. Preferably, the biocompatible polymer material is resorbable and has a high thermal stability. Under conditions utilizing high temperatures, for example in the range of 100 C to 200 C, most biocompatible resorbable will suffer thermal degradation and are therefore unsuitable for use in the described system and processes.

According to the present disclosure, the method includes the step of sealing the first end 11 of the container 100 so as to seal the container cavity 50 from the external environment. In certain embodiments, the container 100 is substantially rigid such that the cavity 50 defines a fixed volume. An exemplary rigid container 100 can be a cylindrical aluminum tube, which is schematically depicted in FIGS. 1A-C. Container According to certain embodiments, the container 100 first end 11 includes a threaded region 13 extending around an outer surface of the container 100, where the threaded region 13 is configured to engage with a lid 80 having a corresponding threaded region 83 on an inner surface, or an outer surface, such that the step of sealing the first end 11 of the container 100 includes engaging the first end threaded region 13 and the lid threaded region 83, for example as shown in FIG. 1B. Embodiments can additionally include a seal member 36 configured to be disposed between and in contact with the lid threaded region 83 and the first end threaded region 13 during the step of sealing. Certain suitable seal members 36 can include for example crush washers or o-rings configured to provide a fluid tight seal.

Figure 2:
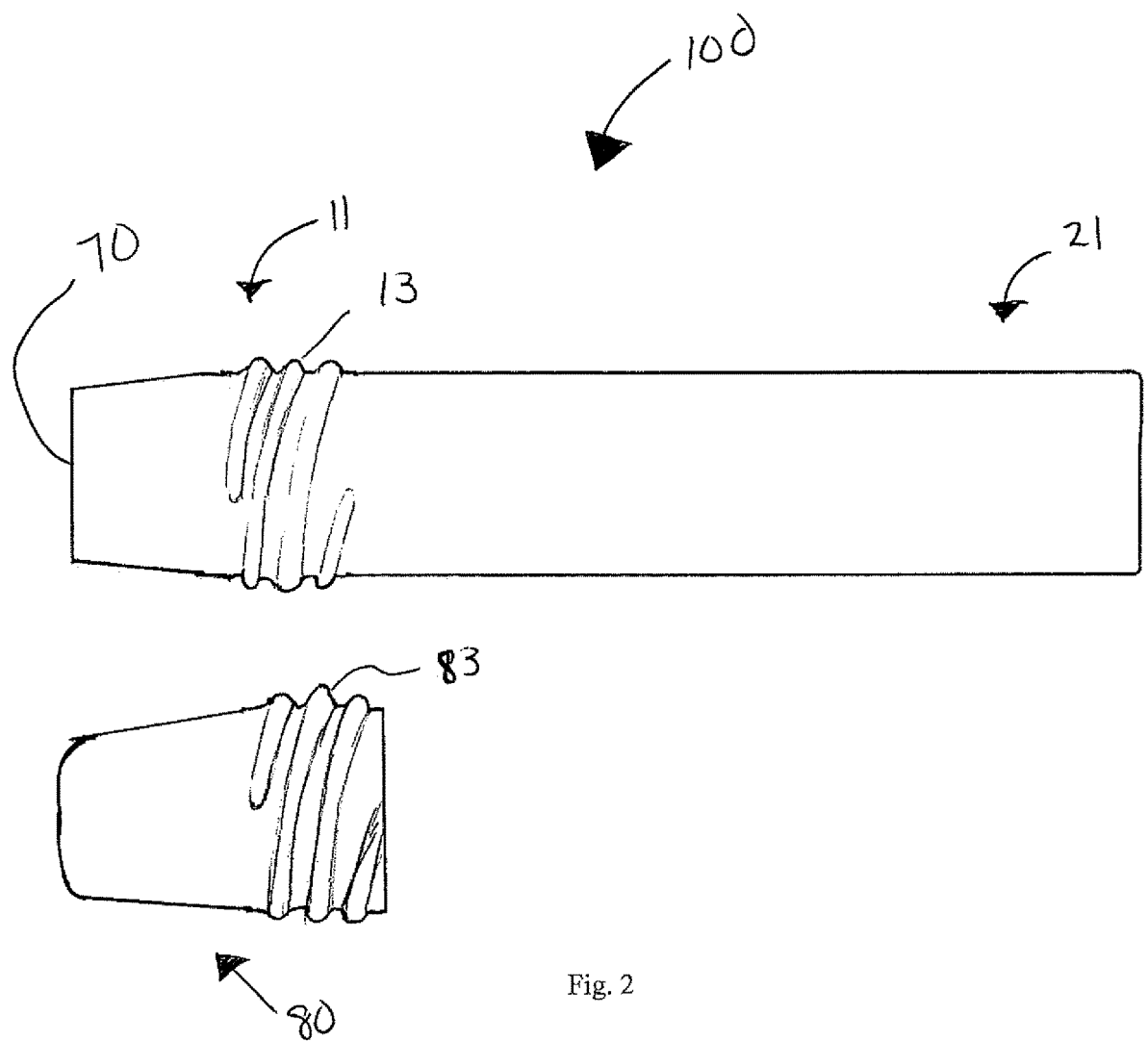
FIG. 2 is side view of a container and lid according to another embodiment of the present disclosure.

With reference to FIG. 2, a substantially rigid container is shown in the general shape of a cigar tube having a tapered first end 11, while lid 80 has a corresponding taper. In addition to the seal formed from the engagement of the respective threaded regions, the taper of the first end 11 and lid 80, can provide a mechanical friction fit engagement, thereby enhancing the seal of the container cavity 50.

Figure 3A:
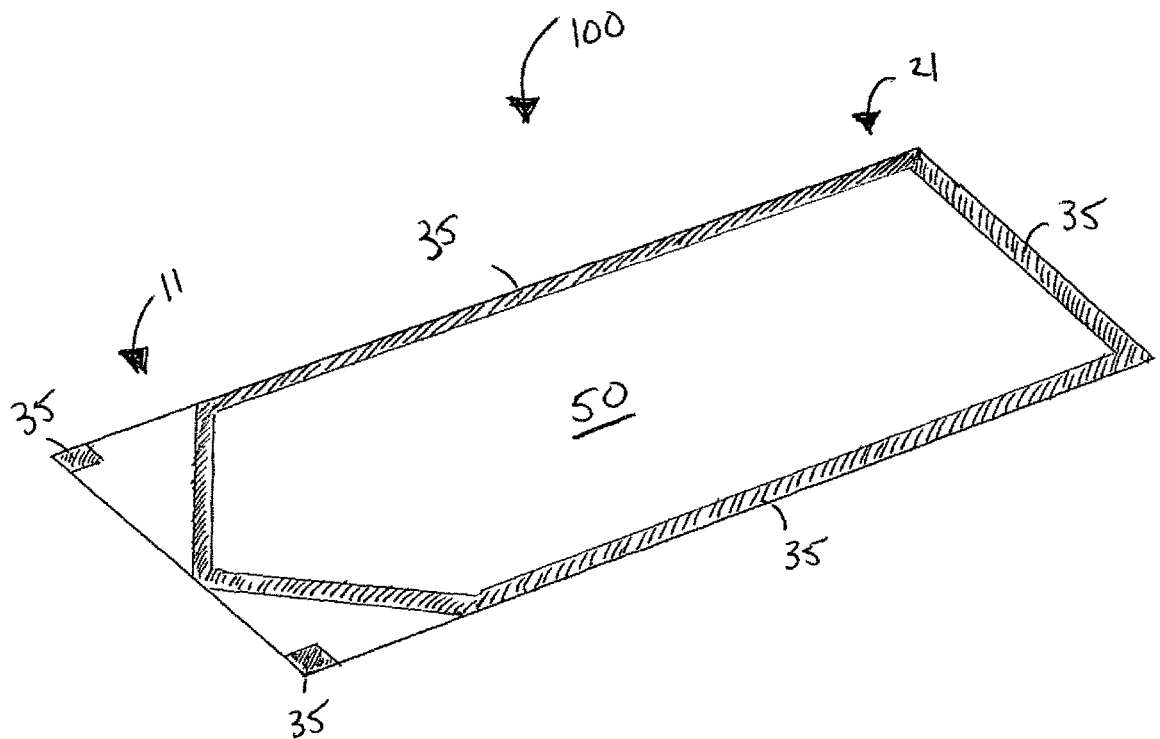
FIG. 3A is a perspective view of a cross-section of an alternate container according to embodiments of the present disclosure.
Figure 3B:
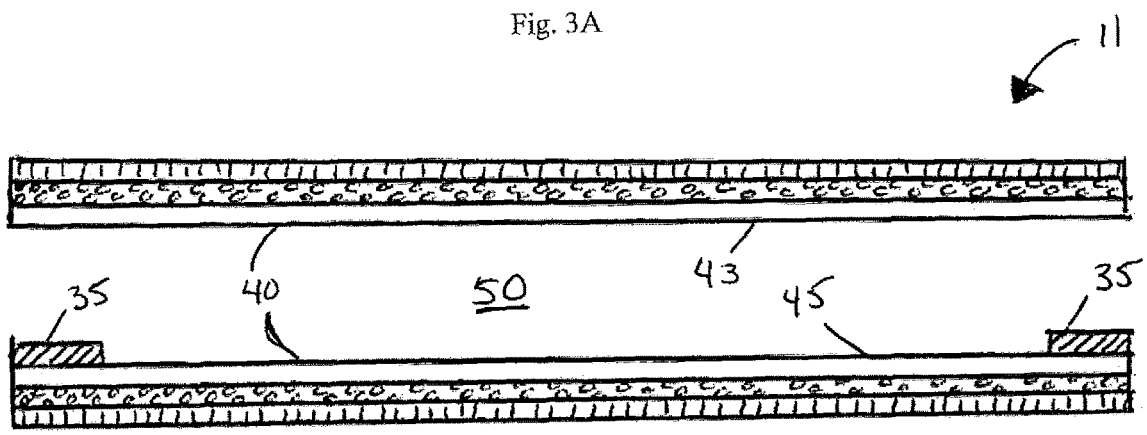
FIG. 3B is side view of the container embodiment according to FIG. 3A.

According to alternative embodiments, and with reference to FIGS. 3-4, the container 100 is substantially deformable and the cavity 50 defines a first geometry having a first volume when the first end 11 is open such that upon deformation the cavity 50 assumes a second geometry having a second volume smaller than the first volume. In certain other embodiments, the first end 11 is substantially deformable, and the step of sealing includes applying pressure to the first end 11 so as to force opposing walls 43, 45 of the inner surface 40 at the first end 11 to contact one another and seal the first end 11. In additional embodiments, at least a portion of the inner surface at the first end 11 includes an amount of sealing agent 35, for example an adhesive agent or thermal bonding agent, such that the upon contact the opposing walls 43, 45 are bonded to one another so as to seal the first end 11. In additional alternative embodiments, the step of sealing can include applying a mechanical fastener to the sealed first end configured to keep the opposing walls in contact with one another.

Figure 5A:
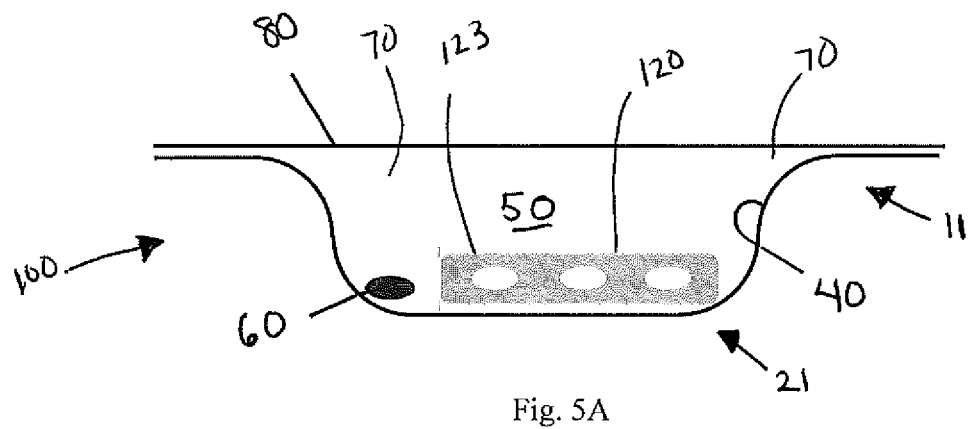
Figure 5B:
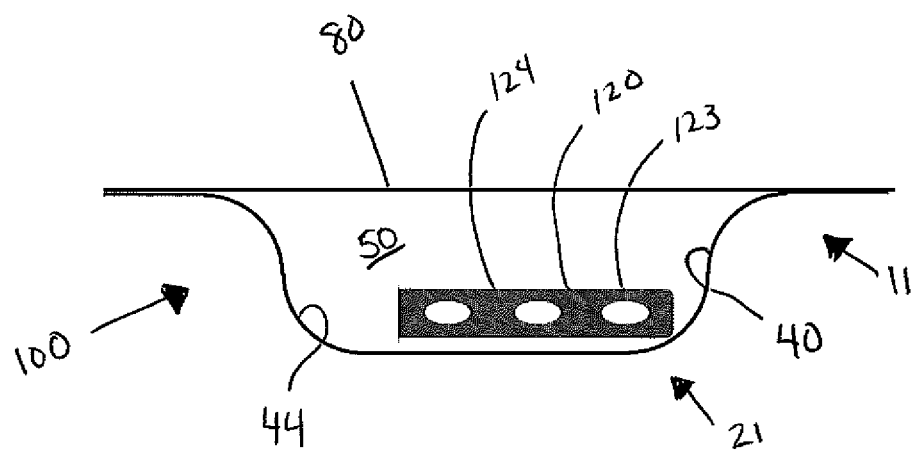

According to still further embodiments, and with reference to FIGS. 5A-B, the container 100 is in the shape of a preformed metal tray (e.g., aluminum or other suitable metal or alloy) having a first end 11 (in this embodiment as shown, the upper portion of the tray) and a second end 21 (in this embodiment as shown, the bottom or base of the tray), and an inner surface 40 extending between the first 11 and second 21 ends. The inner surface 40 includes a material that is non-absorbent to the vaporizable antimicrobial agent, such as a metal, and defines a cavity 50 in the container 100. First end 11 includes an opening 70 extending into the cavity 50, and the cavity further includes the orthopedic implant 120 and a reservoir 60 of vaporizable antimicrobial agent (as shown here, disposed at the base of container 100). Lid 80 is in the form of a metal foil, such as e.g., aluminum. The lid 80 is configured to seal cavity 50 at opening 70. The seal between the container 100 and lid 80 can be achieved for example, by ultrasonic welding of lid 80 to container 100 along the periphery of first end 11. Additionally, the lid 80 can be sealed with container 100 through the use of sealing agents including adhesives or thermal bonding agents. The seal is sufficient to prevent escape of the vaporizable antimicrobial agent, and maintain it within cavity during the process of vapor transfer to the outer surface 124 of the orthopedic implant 120.

According to further embodiments, and with reference to FIGS. 1A-C, the container 100 can include a porous spacer (not shown) at the bottom (i.e., the second end 21), which can act as a stand-off to keep the orthopedic implant 120 from contacting the inner surface at the bottom of the container 100 when the orthopedic implant 120 it is placed inside the container 100. This spacer would allow the reservoir 60 to be placed on the bottom of the container 100 under the spacer or within the pores of the spacer, and prevent contact between the orthopedic implant 120 and the reservoir 60 or otherwise prevent the orthopedic implant 100 from interfering with the vaporization of the antimicrobial agent from the reservoir 60.

In alternative embodiments, the container 100 can be formed (e.g., molded or extruded) from a relatively heat stable polymer such as polypropylene or nylon that could withstand the temperatures of dry heat sterilization. In certain embodiments, container 100 can be rigid, such as shown and described in FIGS. 1-2, or it can be flexible or otherwise deformable, such as shown in FIGS. 3-4. In order to prevent absorption of the antimicrobial agent onto or into the polymer container, the inner surface 40 can be coated with a thin non-polymer layer, such as a silica coating created by chemical vapor deposition. The non-polymer coating for the inner surface 40 of a polymer container 100 may also be aluminum or other suitable metal or alloy that can be coated onto the inner surface 40 by, for example, a vapor deposition or vacuum metallization process.

In further embodiments, where container 100 is flexible (or otherwise deformable), such as is shown in FIGS. 3-4, container 100 may also be formed from a thermally stable polymer such as nylon, and include a thin film of non-polymer material such as aluminum or silica coated onto the inner surface 40 by either a lamination process or vapor deposition process.

According to still further embodiments of a container 100 that is flexible or otherwise deformable container 100, container 100, could be formed as a layered laminated film structure, with an outer layer of heat stable polymer film such as nylon, a middle layer of aluminum foil (or other suitable metal or metal alloy), and the inner surface 40 can include a heat stable polymer film, for example, nylon, where reservoir 60 has been compounded into the film at the inner surface 40. Subjecting the container 100 to a dry heat sterilization process, such as for example 160C for 4 hrs, will cause a portion of the antimicrobial agent in the reservoir 60 at the inner surface 40 to vaporize and subsequently deposit onto the outer surface 123 of the orthopedic implant 120 and form an antimicrobial coating. The interior metal layer in this embodiment acts as a barrier to diffusion of the antimicrobial agent, so that it remain contained inside the container cavity 50.

Returning now to the described method of forming, once the container is sealed, and with reference to FIG. 1C, the method can further include the steps of:
heating the container 100 while sealed so as to heat the outer surface 123 of the orthopedic implant 120 and the reservoir 60 of vaporizable antimicrobial agent so as to cause a vaporization of the antimicrobial agent; and, cooling the container 100 while sealed;
where the heating and cooling of the container 100 causes the vaporized antimicrobial agent to adsorb on the outer surface 123 of the orthopedic implant 120 with respect to the non-absorbent material of the inner surface 40 of the container 100 such that an antimicrobial coated orthopedic implant is formed having a surface area concentration of antimicrobial agent 124 on the outer surface of the orthopedic implant that is sufficient to produce a clinically effective zone of inhibition of at least 0.5 mm from a periphery of the outer surface.

The step of heating can include heating the container to a temperature in the range of about 60 C to 200 C. In a preferred embodiment, the temperature is at least greater than 80 C, for example, in the range of about 80 C to 180 C, or 100 C to 170 C, or 120 C to 160 C, or any combination or subcombination of the temperature range end points listed here. Further the step of heating can occur in the range of about 10 min to about 8 hrs, for example, in the range of about 30 min to about 7 hrs, 1 hr to 6 hrs, 1 hr to 4 hrs, or 2 hrs to 4 hrs, or any combination or subcombination of the disclosed range endpoints listed here. According to certain other embodiments, the heating range can extend up to about 80 hrs, for example 70 hrs, 60 hrs, 50 hrs, 40 hrs, 30 hrs, 20 hrs, or 10 hrs, or from any combination or subcombination of the range endpoints listed here.

Without being bound by any particular theory, it is believed that the utilization of a non-absorbent material along the inner surface of the container enables a greater amount of available vaporizable antimicrobial agent for the outer surface of the orthopedic implant because the container inner surface is not acting as an absorptive sink for the vapor deposition of the vaporizable antimicrobial agent. Further, the sealing of container results in a greater total mass of vaporized antimicrobial agent available for vapor deposition on the outer surface of the orthopedic implant. Finally, the elevated temperatures can also correspond to an increased amount of vaporization of the reservoir than can be achieved in the lower temperature range. Thus the combination of any one of non-absorbent inner surfaces, sealed container systems, and elevated temperatures provided according to the present disclosure are an improvement over the previously described process utilizing standard EO sterilization parameters and allow for a broader selection of orthopedic implants to be formed using antimicrobial vapor deposition such that they can provide a clinically effective ZOI.

Therefore, according to certain embodiments, the antimicrobial coated orthopedic implant includes an antimicrobial coating on the outer surface where the surface area concentration of the antimicrobial agent on the outer surface of the orthopedic implant in the range of about 5 $\mu g/cm^2$ to about 1000 $\mu g/cm^2$, for example in the range of 10 $\mu g/cm^2$ to about 1000 $\mu g/cm^2$, or from about 5 $\mu g/cm^2$ to about 10 $\mu g/cm^2$, or from about 5 $\mu g/cm^2$ to about 100 $\mu g/cm^2$, or from any combination or subcombination of the range endpoints listed here.

In additional embodiments, the antimicrobial agent in the reservoir has a total weight and the vapor deposition causes at least 1% to about 95% of the total weight of the antimicrobial agent to form the antimicrobial coating on the outer surface of the orthopedic implant. Where the outer surface of the orthopedic implant includes a metal or metal alloy, or includes substantially or mostly a metal or metal or metal alloy, the weight percentage of the antimicrobial agent contained in the antimicrobial coating can be at the lower end of the listed weight percentage range. Suitable weight percent ranges for a substantially or mostly entirely metal or metal alloy outer surface can additionally include, for example, 1% to about 20%, or 1% to about 10%, or about 1% to about 5%, or about 5% to about 10%, or about 5% to about 20%, and any combination or subcombination of the range endpoints listed here. Where the outer surface of the implant at least partially or mostly entirely includes a polymer or copolymer the weight percent range can include endpoints of greater than 30% to about 95%, for example 40%, 50%, 60%, 70%, 80%, or 90%.

While the above method has been described in the context of performing a sterilization procedure on an orthopedic implant utilizing the aforementioned high-heat process, it should be appreciated that the method can be applied to peri-operative and intra-operative settings where, in a timeframe near to surgery or during surgery, the recited method steps above can be performed in a surgical suite, or at location near to the location of surgery. The components described above can be provided to the surgeon or a surgical team member as a prepared system (i.e., an already sealed container including the orthopedic implant and the reservoir in the cavity, where only heating and cooling need to be performed to vapor transfer the vaporizable antimicrobial agent onto the outer surface of the implant. Alternatively, the separate components can be provided to be assembled perioperatively, in which case the heating and cooling steps can subsequently be performed after assembly of the components and sealing of the container has been completed according to the above recited steps.

According to the present disclosure, and with reference to FIGS. 1A-B, a system for forming an antimicrobial orthopedic implant as described in the process above includes:

- a reservoir 60 of a vaporizable antimicrobial agent;
- an orthopedic implant 120 defining an outer surface 123; and,
- a container 100 having a first end 11 and a second end 21, and an inner surface 40 extending between the first 11 and second ends 21, the inner surface 40 including a material that is non-absorbent to the vaporizable antimicrobial agent and defining a cavity 50 configured to receive the orthopedic implant 120, where the first end 11 defines a sealable opening 70 extending into the cavity 50;
- where the container 100, the orthopedic implant 120, and the vaporizable antimicrobial agent are configured to remain thermally stable in a temperature range up to 200 C;
- where the reservoir 60 of vaporizable antimicrobial agent is disposed in the container 100;
- where the orthopedic implant 120 is disposed within the cavity 50, and where the outer surface 123 is substantially free of the vaporizable antimicrobial agent.

The presently described system can be considered as embodiments of the present disclosure directed to the arrangement of the recited elements prior to the previously described heating and cooling steps (e.g. as shown in FIGS. 1A-B). It should be understood that features and components and their respective properties, which have been described above in the contest of describing the method of forming the antimicrobial coated implant, apply equally here in describing the individual constituents of the system. For example, the description provided above for the vaporizable antimicrobial agent is considered to be equally applicable in describing the various elements and features of the system. Further, features or sub-features or elements previously described and attributed to the container 100, the orthopedic implant 120, or any other element likewise apply here.

Therefore, the system includes a reservoir 60 of the vaporizable antimicrobial agent, wherein the vaporizable antimicrobial agent comprises halogenated hydroxyl ethers, acyloxydiphenyl ethers, or combinations thereof. In certain embodiments, the vaporizable antimicrobial agent comprises 2,4,4'-trichloro-2'-hydroxydiphenyl ether (triclosan).

According to additional embodiments, the outer surface 123 of the orthopedic implant 120 comprises at least a polyaryletherketone (PAEK) or copolymer thereof, polyalkene or copolymer thereof, or a metal or metal alloy, or a combination thereof. In certain embodiments, the outer surface comprises a metal or metal alloy. Preferably, the metal is titanium, stainless steel, or alloys containing titanium or steel. In certain embodiments, the outer surface comprises a PAEK or copolymer thereof. Preferably, the PAEK is polyetheretherketone (PEEK) or a copolymer thereof. In certain embodiments, the outer surface comprises a polyalkene or copolymer thereof. Preferably, the polyalkene is polyethylene or a copolymer thereof.

In certain embodiments of the system, the container 100 is substantially rigid such that the cavity 50 defines a fixed volume. In certain further embodiments, the first end 11 comprises a threaded region 13 extending around an outer surface of the container 100, wherein the system further comprises a lid 80 having a threaded region 83 configured to engage the first end threaded region 13, such that the engagement of the first end threaded region 13 and the lid threaded region 83 seals the first end 11. In additional embodiments, the system can additionally include a seal member 36 configured to be disposed between and in contact with the lid threaded region 83 and the first end threaded region 13.

In alternative embodiments, the container 100 is substantially deformable and the cavity 50 defines a first geometry having a first volume when the opening 70 at the first end 11 is open, and wherein the container 100 is configured to deform upon application of pressure such that the cavity 50 assumes a second geometry having a second volume smaller than the first volume. In additional embodiments, the first end 11 is substantially deformable such that opposing walls 43, 45 of the inner surface 40 at the first end 11 are configured to contact one another upon application of force to close opening 70 and seal the first end 11. In additional embodiments, at least a portion of the inner surface at the first end 11 includes an amount of sealing agent 35, for example an adhesive agent or thermal bonding agent, such that the upon contact the opposing walls 43, 45 are bonded to one another so as to seal the first end 11. In additional alternative embodiments, the system includes a mechanical fastener configured to keep the opposing walls 43, 45 in contact with one another.

In further embodiments, the second end 21 defines a sealable opening extending into the cavity 50. In some embodiments, the second end 21 is substantially deformable such that opposing walls 43, 45 of the inner surface 40 at the second end are configured to contact one another upon application of force and seal the second end.

According to the present disclosure, and with reference to FIG. 1C, a packaging configuration for a sterile antimicrobial orthopedic implant is described including:

- a sealed sterile container having a first end and a second end, and an inner surface extending between the first and second ends, the inner surface defining a cavity, where the first end defines a sealable opening extending into the cavity;
- a sterile orthopedic implant disposed in the cavity, the orthopedic implant defining an outer surface;
- where the orthopedic implant has an antimicrobial coating on the outer surface, the antimicrobial coating including a surface area concentration of a vaporizable antimicrobial agent on the outer surface of the orthopedic implant;
- wherein the inner surface comprises a material that is non-absorbent to the vaporizable antimicrobial agent; and,
- where the inner surface has a surface area concentration of the vaporizable antimicrobial agent in the range of about 5 μg/cm$^2$ to about 1000 μg/cm$^2$.

The presently described packaging configuration can be considered as directed to embodiments concerning the arrangements and features of the recited elements after the dry heat sterilization and vapor deposition process has been completed and the antimicrobial coating has been formed on the outer surface of the orthopedic implant.

According to certain embodiments, the vaporizable antimicrobial agent of the antimicrobial coating comprises halogenated hydroxyl ethers, acyloxydiphenyl ethers, or combinations thereof. In preferred embodiments, the vaporizable antimicrobial agent comprises 2,4,4'-trichloro-2'-hydroxydiphenyl ether (triclosan).

According to additional embodiments, the outer surface 123 of the orthopedic implant 120 comprises at least a polyaryletherketone (PAEK) or copolymer thereof, polyalkene or copolymer thereof, or a metal or metal alloy, or a combination thereof. In certain embodiments, the outer surface comprises a metal or metal alloy. Preferably, the metal is titanium, stainless steel, or alloys containing titanium or steel. In certain embodiments, the outer surface comprises a PAEK or copolymer thereof. Preferably, the PAEK is polyetheretherketone (PEEK) or a copolymer thereof. In certain embodiments, the outer surface comprises a polyalkene or copolymer thereof. Preferably, the polyalkene is polyethylene or a copolymer thereof.

According to certain embodiments, the first end 11 comprises a threaded region 13 extending around an outer surface of the container 100, wherein the packaging configuration further comprises a lid 80 having a threaded region 83 engaged with the first end threaded region 13, such that the first end 11 is sealed. In additional embodiments, the system can additionally include a seal member 36, such as a crush washer or an O-ring, disposed between and in contact with the lid threaded region 83 and the first end threaded region 13.

Figure 4A:
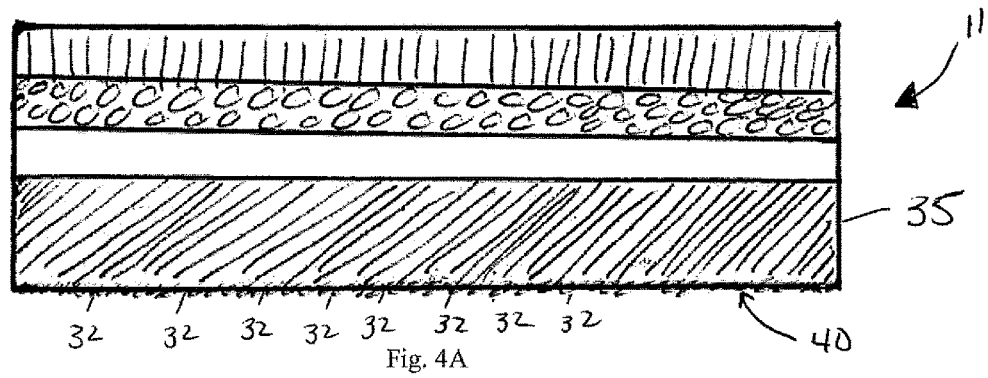
FIGS. 4A-B are cross-sectional side views of an alternate container according to the present disclosure; and, FIGS. 5A-B are cross sectional side views of an another container embodiment according to the present disclosure.
Figure 4B:
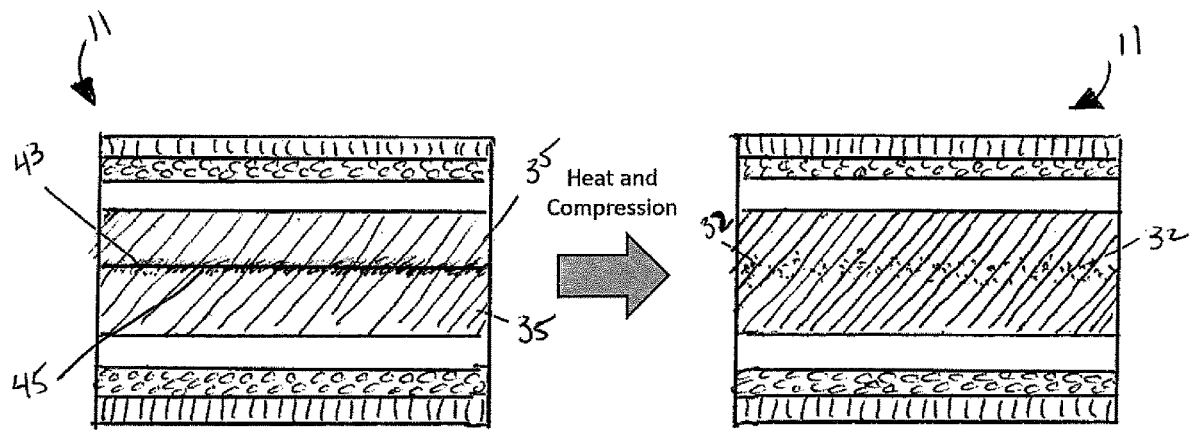

In further embodiments, for example as shown in FIGS. 4A-B, at least a portion of the inner surface 40 at the first end 11 comprises an amount of sealing agent 35 bonding the opposing walls 43, 45 to one another so as to seal the first end 11. The sealing agent 35 can include, for example, an adhesive material or a thermal bonding material. In additional embodiments, the packaging configuration can include a mechanical fastener applied to the opposing walls 43, 45 so as to keep them in contact with one another sealing the container 100.

According to certain embodiment, the antimicrobial coated orthopedic implant includes an antimicrobial coating on the outer surface where the surface area concentration of the antimicrobial agent on the outer surface of the orthopedic implant in the range of about 5 $\mu g/cm^2$ to about 1000 $\mu g/cm^2$. In additional embodiments, the vaporizable antimicrobial agent in the container has a total weight and at least 1% of the total weight of the vaporizable antimicrobial agent is contained in the antimicrobial coating on the orthopedic implant.

According to the present disclosure, an antimicrobial coated implant is described including:
- an orthopedic implant, the orthopedic implant defining an outer surface consisting essentially of a metal or metal alloy, a polyalkene or copolymer thereof, or a polyaryletherketone or copolymer thereof, or a combination thereof; and,
- an antimicrobial coating disposed on the outer surface of the orthopedic implant, the antimicrobial implant consisting essentially of a vaporizable antimicrobial agent;
- where the antimicrobial coated implant has a surface area concentration of antimicrobial agent on the outer surface of the orthopedic implant in the range of about 5 $\mu g/cm^2$ to about 1000 $\mu g/cm^2$; and,
- where the surface area concentration produces a clinically effective zone of inhibition against microbial forming units of at least 0.5 mm from the outer surface of the orthopedic implant.

According to certain embodiments, the outer surface is a metal or metal alloy. In preferred embodiments, the metal or metal alloy is titanium or stainless steel or alloys thereof. According to certain embodiments, the outer surface is a polyalkene or copolymer thereof. In preferred embodiments, the polyalkene is polyethylene or a copolymer thereof. According to certain embodiments, the outer surface is a PAEK or copolymer thereof. In preferred embodiments, the PAEK is polyetheretherketone (PEEK).

According to certain embodiments, the outer surface includes a combination of the previously recited materials. For example, in certain embodiments, the outer surface consists essentially of a metal or metal alloy, and a polyalkene or copolymer thereof. Preferably, the outer surface consists essentially of titanium or stainless steel or alloys thereof, and polyethylene or copolymers thereof. In certain alternative embodiments, the outer surface consists essentially of a metal or metal alloy, and a polyaryletherketone or copolymer thereof. Preferably, the outer surface consists essentially of titanium or stainless steel or alloys thereof, and PEEK or copolymers thereof. In certain further alternative embodiments, the outer surface consists essentially of polyalkene or copolymer thereof, and a polyaryletherketone or copolymer thereof. Preferably, the outer surface consists essentially of polyethylene or copolymer thereof, and PEEK or copolymer thereof.

According to certain embodiments, the vaporizable antimicrobial agent comprises halogenated hydroxyl ethers, acyloxydiphenyl ethers, or combinations thereof. Preferably, the vaporizable antimicrobial agent comprises 2,4,4'-trichloro-2'-hydroxydiphenyl ether (triclosan).

According to additional embodiments, the antimicrobial coating produces surface area concentration on the outer surface of the orthopedic implant in the range of 10 $\mu g/cm^2$ to about 1000 $\mu g/cm^2$.

Accord to still additional embodiments, the effective ZOI of the antimicrobial coated implant is in the range of about 0.5 mm to about 5.0 mm.

EXAMPLES

In the following examples, unless otherwise stated, ethylene oxide (EO) sterilization conditions (or "processes" or "parameters" or the like) refers to exposure of the implant to 55 C for 15 minutes at ambient pressure, then exposure to 55 C under vacuum for an additional 3 hours 45 minutes.

Example 1

Vapor transfer of triclosan on to metal orthopedic implants was attempted according to the process described in U.S. Pat. No. 8,668,867 to see if the process described could effectively deposit triclosan onto a metal surface.

A series of metal pins (approximately 4 mm×30 mm) including 1) titanium alloy (Ti-6Al-7Nb (TAN)), 2) 316L Stainless Steel, and, 3) TAN pins having poly(D,L-lactide) (PLA) coating at about 0.55 mg/cm² were tested.

Triclosan (IRGACARE MP Triclosan Lot #0013227542) was compounded at 2.56% by weight into a sheet of High Density Polyethylene (HDPE).

The pins were copackaged with 0.62 to 0.66 grams of triclosan impregnated HDPE sheet (approximately 16 mg of triclosan) into a 4-layer packaging material suitable for EO sterilization that had an outer PET layer, a polyethylene layer, a foil moisture barrier, and an inner polyethylene heat-sealing layer, with a foil layer (moisture barrier) disposed in between the two. The package was sterilized, and underwent a heat treatment at 55° C. for 4 hours.

After the EO sterilization process was completed, the pins were measured for anti-bacterial activity. *S. aureus* at 3.03× $10^9$ CFU/mL was spread on pre-formed plate by sterile cotton swab, and the pins were gently pressed into the surface of spread plate, but not penetrating agar. The plates were incubated for 24 hours and then ZOIs measured for each pin.

Total Zone was measured across the width (short axis) of the implant and the results were as follows:
  Stainless: minimal observed zone of reduced growth (no ZOI);
  TAN: minimal observed zone of reduced growth (no ZOI); and
  TAN-PLA: 12.4 mm ZOI.

Accounting for the implant width (~4.0 mm) and dividing by 2 to account for the ZOI on each side of the implant, the ZOI around the perimeter for each implant type was:
  Stainless: Not observed;
  TAN: Not observed; and
  TAN-PLA: ~4.2 mm.

Thus, the results showed that only the polymer coated pins (TAN-PLA) were able to provide a clinically effective ZOI and the pins with only a metal substrate surface were unable to retain a clinically significant amount of triclosan.

Example 2

The following test was conducted in view of Example 1 to identify ways to increase transfer of triclosan to metal substrate surfaces. Metal implants that had been subjected to alkaline surface treatments were treated with triclosan by a dry-heat transfer process in packaging having a substantially metallic inner surface. Triclosan content was measured through a UV assay.

The implants used in this test were TAN anodized pins (4.0 mm×30 mm). The alkaline treatment composition was potassium hydroxide (KOH) for 4 hours. The implants were then subject to triclosan vapor deposition under high-heat conditions in a container having an aluminum inner surface. Additional control samples were subjected to triclosan vapor deposition according to the process previously described in Example 1 in order to compare the results.

Alkaline Treatment

The samples were washed in 1% Alconox, scrubbed clean with a brush and then washed with DI water. The samples were then placed together in a beaker and 300 mL of DI water was added and the heated to boiling for 15 min. The beaker was then allowed to cool, and the samples were removed and placed on crumpled aluminum foil to air dry.

A 6M KOH solution was prepared in a Nalgene plastic bottle with lid. 12 TAN anodized pins (4.0 mm×30 mm) were placed in the bottle and the lid placed on loosely to prevent gas buildup. The bottle was placed in an oven at 60° C. for 4 hours.

After the KOH treatment was finished, the solution was removed from the bottle and the samples remained. The bottles were rinsed 3× with DI water and then samples were soaked in PBS for approximately 5 min. The PBS was removed and each bottle was again washed 3× with DI water. The samples were then removed from their respective bottles and placed on crumpled aluminum foil until dry.

Triclosan Vapor Deposition—Aluminum Bottle with Aluminum Foil Seal

A Triclosan/Ethyl Acetate mixture was prepared by weighing 60 mg of triclosan and placing it into the aluminum bottle along with 0.5 mL of ethyl acetate and swirling the bottle. The lid was left off of the bottle and it was allowed to air dry overnight.

The samples were then placed in the bottles and hung in place using a steel wire frame.

Once the samples were in place, multiple layers of aluminum foil were placed over the bottle opening and crumpled tightly to form a seal. The seal was reinforced by wrapping steel wire around the foil lid.

The sample bottles were place in a 160 C oven for about 4 hrs.

Following triclosan transfer, the amount of triclosan transferred to the metal pin was quantified by UV spectrophotometry.

UV Method

Triclosan standards were prepared from an initial mass of triclosan weighed into a volumetric flask and dissolved in 10 mL of solvent (100% Acetonitrile). This stock solution of triclosan was used to prepare standards in 10 mL volumetric flasks and covered with foil to protect from light.

Samples of 1 mL were then transferred to plastic cuvettes and analyzed with UV at 280 nm on a NanoDrop 2000c Spectrophotometer. After a standard curve was created by plotting absorbance at 280 nm vs. triclosan concentrations, the implant samples from above were then analyzed.

Sample Preparation

Triclosan treated samples were placed in sterile 15 mL centrifuge tubes. 2.5 mL of acetonitrile was added to each tube, then tubes were placed on the shaker incubator. The tubes were shaken for 24 hr at 250 rpm, then the pins were transferred into a separate sterile tube. The sample solution was stored at 4° C. until analyzed. For analysis, 15 ml centrifuge tubes containing the sample were vortexed briefly. 1 mL of the sample was then analyzed with the UV Nanodrop instrument at 280 nm wavelength and the concentration of each sample was determined from the constructed standard curve. Samples which showed very high initial concentration were diluted 1:10 with Acetonitrile.

TABLE 1 results of UV testing

| Sample | Triclosan dose in package (mg) | Triclosan dose in package per pin (mg) | Triclosan transferred to pin (mg) | Triclosan transferred per area (μg/cm2) | % triclosan on pin |
|---|---|---|---|---|---|
| 160° C. oven, aluminum container (4 pins) | 59.7 | 14.9 | 1.504 | 374 | 10% |
| 55° C. oven, foil header pouch (1 pin) | 19.9 | 19.9 | 0.027 | 6.7 | 0.14% |

The 4 mm×30 mm 4-hour alkaline treated anodized TAN pin had 1.50 mg of triclosan on its surface when triclosan transfer was performed in an all-metal container at 160 C for 4 hours. In contrast, only 0.027 mg of triclosan was observed on the same sample with triclosan transfer conducted from a sleeve in a foil pouch at 55 C. Thus, comparing the same metal substrate and alkalizing conditions it can be seen that dry heat closed metal container produced a greater than 55 time increase in triclosan on the implant surface as compared to the EO sterilization conditions.

Example 3: Cooling Rate for High Heat Transfer Process

This experiment was conducted to determine if the cooling rate after performing the dry heat transfer process in the aluminium container as described in Example 2 affects the vapor deposition of triclosan onto the TAN pins. This experiment measured any difference in vapor deposition between leaving pins in the hot oven as it cools versus placing them immediately on a cold counter top to cool.

The aluminium bottle containers were first cleaned with IPA and ethyl acetate and allowed to dry. Next, 2 mg of triclosan was placed inside each bottle. A porous stainless steel metal mesh was placed in the bottom of each container to act as a stand-off for the pins keeping them from directly contacting the triclosan reservoir.

TAN pins were placed in the containers at 1 pin per container. The aluminium containers were sealed with a lid and included an aluminium crush washer each.

The bottles were placed in an oven and heated to 160 C for 4 hours.

After the heat cycle was completed, the ovens were shut off. Half of the bottles were immediately removed from the oven and place on a cold countertop and the remainder were left in the oven.

Table 2 below shows the reservoir weight of the triclosan prior to initiating heating, the initial mass of the system, and the final mass of the system after cooling was completed. System mass loss was recorded as the difference between the initial and final masses of the sample, and can be attributed only to the loss of vaporized triclosan from the container during wino either heating or cooling.

TABLE 2

Triclosan mass balance during heating and cooling

| Sample | Triclosan Dose [mg] | System mass [mg] Initial | System mass [mg] Final | Mass loss [mg] | Average loss [mg] | t-test |
|---|---|---|---|---|---|---|
| Fast Cool 1 | 2.14 | 11913.86 | 11913.31 | 0.55 | 1.03 | 0.40 |
| Fast Cool 2 | 2.16 | 11954.94 | 11953.06 | 1.88 | | |
| Fast Cool 3 | 2.29 | 11819.87 | 11819.22 | 0.65 | | |
| Slow Cool 1 | 2.19 | 11816.11 | 11815.38 | 0.73 | 0.57 | |
| Slow Cool 2 | 2.19 | 15788.48 | 15788.01 | 0.47 | | |
| Slow Cool 3 | 2.07 | 11958.34 | 11957.82 | 0.52 | | |

The sample pins were additionally measured for surface triclosan content through UV analysis in the same manner as previously described in Example 2. The UV data is shown below in Table 3.

TABLE 3

Tricolsan transferred to pins by UV analysis

| Sample name | Dose by mass balance | Triclosan on Pins by UV | Triclosan in Bottles by UV | % dose on Pin | Triclosan per area [µg/cm$^2$] |
|---|---|---|---|---|---|
| Fast Cool 1 | 2.14 | 0.17 | 1.81 | 8% | 42 |
| Fast Cool 2 | 2.16 | 0.05 | 1.97 | 2% | 13 |
| Fast Cool 3 | 2.29 | 0.09 | 2.02 | 4% | 22 |
| Slow Cool 1 | 2.19 | 0.11 | 2.04 | 5% | 27 |
| Slow Cool 2 | 2.19 | 0.16 | 2.39 | 7% | 40 |
| Slow Cool 3 | 2.07 | 0.12 | 2.37 | 6% | 30 |
| Ave Fast Cool | 2.20 | 0.10 | 1.94 | 5% | 26 |
| StDev Fast Cool | 0.08 | 0.06 | 0.11 | 3% | 15 |
| Ave Slow Cool | 2.15 | 0.13 | 2.27 | 6% | 32 |
| StDev Slow Cool | 0.07 | 0.03 | 0.20 | 1% | 7 |

Example 4: Alkaline v Non-Alkaline Dry Heat Treatment

The purpose of this experiment was to evaluate the effects of the alkaline treatment on the TAN pins described in Example 2. Untreated electropolished stainless steel pins were added to this study to provide a reference to the observed effects of alkaline treatment of the TAN pins. This study used the same parameters as Example 2 of dosing alkaline treated and untreated TAN pins with ⅔ mg, 2 mg, or 6 mg of triclosan. The results were measured with UV analysis as described in Example 2. In this example, triclosan dosing was varied to observe whether the implant can still adsorb effective amounts of triclosan with a relatively low mass of reservoir in the container system.

Alkaline Treated Samples

The pins receiving alkaline treatment underwent the same process as described in Example 2 for an 8 hour alkaline treatment.

Triclosan Reservoir Preparation

The aluminium bottle containers were washed and cleaned with IPA and ethyl acetate.

A triclosan solution was prepared by adding 48 mg of triclosan into 800 µl of ethyl acetate (60 mg/ml).

Into bottles receiving the ⅔ mg dose, 10 µl of solution was placed, for bottles receiving a 2 mg dose, 30 µl, and for the bottles receiving the 6 mg dose, 90 µl. Each bottle then had ethyl acetate added to bring the total volume in each container to 100 µL.

Each container was left unsealed and allowed to dry overnight.

As described in Example, each container had a metal mesh offset placed in the bottom of the container. The pins were then added to the containers at 1 pin per bottle. The bottles were then sealed with the lids and included aluminium crush washers.

The sample were then loaded into the oven at 160 C for 4 hours.

Table 4 below, shows the target dose applied to each container, the amount of triclosan in each container, measured by mass difference, the amount of triclosan on each implant after the dry heat transfer process as measured by the UV methods previously described, and the calculated amount of triclosan on each pin as a weight percent of the measured original amount of triclosan in the reservoir.

TABLE 4

Triclosan transfer analysis for increasing triclosan doses and three target materials

|  | Target dose [mg] | Actual dose [mg] | Average on Pin [mg] | StDev [mg] | % of dose | Dose per area [μg/cm²] |
|---|---|---|---|---|---|---|
| TAN | 0.67 | 0.60 | 0.021 | 0.006 | 3.5% | 5.3 |
|  | 2 | 1.92 | 0.119 | 0.025 | 6.2% | 29.7 |
|  | 6 | 5.67 | 0.597 | 0.017 | 10.5% | 148 |
| 8-hour alkaline-treated TAN | 0.67 | 0.56 | 0.057 | 0.023 | 10.2% | 14.1 |
|  | 2 | 1.84 | 0.121 | 0.010 | 6.6% | 30.0 |
|  | 6 | 5.47 | 0.701 | 0.644 | 12.8% | 174 |
| Stainless Steel | 0.67 | No Data | 0.002 | 0.008 | 0.3% | 0.5 |
|  | 2 | 2.02 | 0.083 | 0.043 | 4.1% | 20.7 |
|  | 6 | 6.00 | 0.138 | 0.106 | 2.3% | 34.4 |

These results indicate that while alkaline treatment improved triclosan adsorption onto the TAN pins, it was not statistically meaningful. These tests further confirmed that irrespective of the metal substrate surface, increasing dosing at lower limits, correspondingly increased the amount of triclosan transferred onto the implant outer surface.

Example 5: High Heat Triclosan Transfer v. Implant Surface Comparison

This experiment was conducted to further examine the triclosan vapor transfer under dry heat v. EO sterilization process conditions, such as was previously done in Example 2. Additionally, in this test, PEEK was added as an implant surface substrate. As previously noted, it is surmised that under EO sterilization conditions, a polymer substrate surface has a high enough affinity for triclosan to offset the loss of reservoir mass and still absorb sufficient quantities. This test will directly compare the ability of the dry heat transfer process to deposit triclosan onto a PEEK surface as compared to a transfer process under EO sterilization conditions. Further, in both Example 1 and Example 2, implants with a metal substrate surface failed to achieve a meaningful amount of triclosan on the surface under the EO sterilization transfer process.

In this experiment, for each implant material and transfer condition, samples will be tested for triclosan content, both by UV analysis and ZOI measurements utilizing a pour plate protocol with S. aureus in agar pour plates. Additionally, samples will be tested immediately after the vapor transfer process is completed, as well after being immersed in a PBS solution for one hour and 24 hour to measure the robustness of the antimicrobial coating on each sample surface.

Below, Table 5 shows the samples used in this test, identified by implant material type (e.g., steel, TAN, or PEEK), transfer condition (EO pouch method or high-heat bottle method), and elution time. The table is broken down into sample ID by UV analysis samples and ZOI analysis samples.

TABLE 5

Triclosan Content - UV analysis

| Material | Sample Number | Sample ID | Enclosure | Elution time |
|---|---|---|---|---|
| Anodized 4.0 MM TAN Pin | 1 | TP0-1 | Pouch | Immediate |
|  | 2 | TP0-2 |  | Immediate |
|  | 3 | TP1-1 |  | 1 hr |
|  | 4 | TP1-2 |  | 1 hr |
|  | 5 | TP24-1 |  | 24 hr |
|  | 6 | TP24-2 |  | 24 hr |
|  | 7 | TB0-1 | Bottle | Immediate |
|  | 8 | TB0-2 |  | Immediate |
|  | 9 | TB1-1 |  | 1 hr |
|  | 10 | TB1-2 |  | 1 hr |
|  | 11 | TB24-1 |  | 24 hr |
|  | 12 | TB24-2 |  | 24 hr |
| Electropolished Stainless Steel 4.0 MM Pin | 13 | SP0-1 | Pouch | Immediate |
|  | 14 | SP0-2 |  | Immediate |
|  | 15 | SP1-1 |  | 1 hr |
|  | 16 | SP1-2 |  | 1 hr |
|  | 17 | SP24-1 |  | 24 hr |
|  | 18 | SP24-2 |  | 24 hr |
|  | 19 | SB0-1 | Bottle | Immediate |
|  | 20 | SB0-2 |  | Immediate |
|  | 21 | SB1-1 |  | 1 hr |
|  | 22 | SB1-2 |  | 1 hr |
|  | 23 | SB24-1 |  | 24 hr |
|  | 24 | SB24-2 |  | 24 hr |
| PEEK Rods | 25 | PP0-1 | Pouch | Immediate |
|  | 26 | PP0-2 |  | Immediate |
|  | 27 | PP1-1 |  | 1 hr |
|  | 28 | PP1-2 |  | 1 hr |
|  | 29 | PP24-1 |  | 24 hr |
|  | 30 | PP24-2 |  | 24 hr |
|  | 31 | PB0-1 | Bottle | Immediate |
|  | 32 | PB0-2 |  | Immediate |
|  | 33 | PB1-1 |  | 1 hr |
|  | 34 | PB1-2 |  | 1 hr |
|  | 35 | PB24-1 |  | 24 hr |
|  | 36 | PB24-2 |  | 24 hr |

Triclosan Content - ZOI

| Material | Sample Number | Sample ID | Matrix Material | Pre-elution |
|---|---|---|---|---|
| Anodized 4.0 MM TAN Pin | 1 | TP0-3 | Pouch | Immediate |
|  | 2 | TP1-3 |  | 1 hr |
|  | 3 | TP24-3 |  | 24 hr |
|  | 4 | TB0-3 | Bottle | Immediate |
|  | 5 | TB1-3 |  | 1 hr |
|  | 6 | TB24-3 |  | 24 hr |
| Electropolished Stainless Steel 4.0 MM Pin- NRD.16.2857.102379 | 7 | SP0-3 | Pouch | Immediate |
|  | 8 | SP1-3 |  | 1 hr |
|  | 9 | SP24-3 |  | 24 hr |
|  | 10 | SB0-3 | Bottle | Immediate |
|  | 11 | SB1-3 |  | 1 hr |
|  | 12 | SB24-3 |  | 24 hr |
| PEEK Rods | 13 | PP0-3 | Pouch | Immediate |
|  | 14 | PP1-3 |  | 1 hr |
|  | 15 | PP24-3 |  | 24 hr |
|  | 16 | PB0-3 | Bottle | Immediate |
|  | 17 | PB1-3 |  | 1 hr |
|  | 18 | PB24-3 |  | 24 hr |

Table 6, shown below shows a relative comparison of triclosan dosing, package material, temperature and time parameters, sample surface substrate, post processing testing conditions, and measurement parameters for both UV and ZOI analysis.

TABLE 6

| Parameter | EO pouch transfer | High Heat bottle transfer |
|---|---|---|
| Dose | PE-Tyvek 13.6 ± 1.1 mg triclosan | 1.86 ± 0.08 mg triclosan |
| Container | Foil header pouch | Screw-cap aluminum bottle with aluminum washer |
| Exposure | 55 C. 4 hours, 15 min atmospheric pressure, 15 min active vacuum, 3.5 hrs static vacuum | 4 hours 160 C. atmospheric pressure |
| Samples | 4 mm diameter × 30 mm long pins of Electropolished stainless steel, Anodized TAN, and PEEK | |
| Pre-elute samples | Samples were either evaluated immediately upon removing from the package or pre-eluted for 1 or 24 hours | |
| Triclosan on test article, UV method | Acetonitrile extraction for 2 hours, read UV absorbance at 280 nm. N = 2 for each material, container/exposure, and pre-elution timepoint | |
| ZOI method | $10^5$ ATCC 25923 S. Aureus in agar pour plates; agar containing bacteria is poured around the implants in a sterile petri dish. The bacteria are allowed to grow for 24 hours at 37 C. A photograph is taken of each plate and the zone is measured using NIH ImageJ. The size of the zone is measured in pixels as the margin from the edge of the device to the edge of the zone of bacterial growth inhibition on four sides of the sample. The diameter of the pin is measured in pixels to calculate the number of pixels per 4 mm. The zone size is calculated by dividing the average zone margin in pixels by the number of pixels per mm. | |

TABLE 7

Triclosan on pin by acetonitrile extraction and UV analysis

| Pin Type | Time in PBS (hrs) | Treated in Pouch Triclosan [mg] Average | StDev | Treated in Bottle Triclosan [mg] Average | StDev | Fold increase of triclosan in bottle |
|---|---|---|---|---|---|---|
| TAN | 0 | 0.011 | 0.009 | 0.17 | 0.02 | 15.3 |
|  | 1 | 0.017 | 0.018 | 0.13 | 0.03 | 7.9 |
|  | 24 | 0.006 | 0.001 | 0.03 | 0.00 | 4.3 |
| Stainless Steel | 0 | 0.005 | 0.000 | 0.36 | 0.19 | 68.1 |
|  | 1 | 0.014 | 0.004 | 0.32 | 0.02 | 22.8 |
|  | 24 | 0.012 | 0.000 | 0.12 | 0.04 | 9.9 |
| PEEK | 0 | 0.008 | 0.002 | 0.21 | 0.00 | 25.2 |
|  | 1 | 0.010 | 0.005 | 0.17 | 0.03 | 18.0 |
|  | 24 | 0.004 | 0.000 | 0.12 | 0.04 | 30.9 |

TABLE 8

Average triclosan per container by UV analysis

| Pin Type | | Time in PBS (hrs) | Triclosan [mg] Average | StDev | Triclosan per area [µg/cm²] | % Triclosan |
|---|---|---|---|---|---|---|
| Pouch | TAN | | 0.011 | 0.009 | 2.74 | 0.08% |
|  | Stainless Steel | | 0.005 | 0.000 | 1.32 | 0.04% |
|  | PEEK | | 0.008 | 0.002 | 2.03 | 0.06% |
| Bottle | TAN | | 0.17 | 0.02 | 41.8 | 9.0% |
|  | Stainless Steel | | 0.36 | 0.19 | 90.1 | 19.3% |
|  | PEEK | | 0.21 | 0.00 | 51.2 | 10.8% |

TABLE 9

Zone of Inhibition by pour plate method

| Pin Type | Time in PBS (hrs) | Pouch ZOI [mm] | Bottle ZOI [mm] |
|---|---|---|---|
| TAN | 0 | 0.8 | 2.8 |
|  | 1 | 0 | 2.2 |
|  | 24 | 0.9 | 0 |
| Stainless Steel | 0 | 0 | 2.8 |
|  | 1 | 0 | 2.3 |
|  | 24 | 0 | 1.6 |
| PEEK | 0 | 2.2 | 1.7 |
|  | 1 | 1 | 1.1 |
|  | 24 | 0 | 0.7 |

As can be seen in the tables, with all materials, the initial triclosan transferred to the target devices was greater than 10-fold higher in the non-absorbent package at 160° C. as compared to EO pouch. This is despite the fact that the total triclosan in metal bottle container was 1.86 mg, while the EO pouch package contained 13.6 mg of triclosan. For metal samples, this resulted in effective ZOIs in the range of greater than 2 mm initially and after 1 hour, while ZOIs produced by samples in EO pouch containers were less than 1 mm for the TAN pins and were not distinguishable for electropolished stainless steel. The PEEK sample had greater than 10-fold more triclosan at all time points, demonstrating a sustained reservoir of triclosan after implantation, though ZOIs were similar when either sample was immediately placed in the pour plate or was if the sample was pre-eluted for 1 hour. The observance of ZOIs in the high-heat PEEK sample at 24 hours (0.7 mm) versus no zone from the conventionally-treated PEEK sample may be due to the ongoing reservoir of triclosan remaining after 24 hours of pre-elution (0.12 mg versus 0.004 mg).

The invention claimed is:

1. A system for forming an antimicrobial implant comprising:
   a reservoir of a vaporizable antimicrobial agent;
   an orthopedic implant defining an outer surface; and,
   a container having a first end and a second end, and an inner surface extending between the first and second ends, the inner surface defining a cavity configured to receive the orthopedic implant, wherein the first end defines a sealable opening extending into the cavity;
   wherein the inner surface comprises a material that is non-absorbent to the vaporizable antimicrobial agent;
   wherein the container, the orthopedic implant, and the vaporizable antimicrobial agent are configured to remain thermally stable in a temperature range up to 200° C.;
   wherein the reservoir of vaporizable antimicrobial agent is disposed in the container;
   wherein the orthopedic implant is disposed within the cavity, and wherein the outer surface is substantially free of the vaporizable antimicrobial agent; and,
   wherein the vaporizable antimicrobial agent is in fluid communication with the orthopedic implant within the container but does not adsorb onto the outer surface of the orthopedic implant until the vaporizable antimicrobial agent is vaporized by heating.

2. The system of claim 1, wherein the vaporizable antimicrobial agent comprises halogenated hydroxyl ethers, acyloxydiphenyl ethers, or combinations thereof.

3. The system of claim 2, wherein the vaporizable antimicrobial agent comprises 2,4,4'-trichloro-2'-hydroxydiphenyl ether (triclosan).

4. The system of claim 1, wherein the outer surface of the orthopedic implant comprises at least a polyaryletherketone (PAEK), polyalkene, or a metal or metal alloy, or a combination thereof.

5. The system of claim 4, wherein the outer surface comprises a metal or metal alloy.

6. The system of claim 5, wherein the metal is titanium, stainless steel, or alloys containing titanium or steel.

7. The system of claim 4, wherein the PAEK is polyetheretherketone (PEEK) or a copolymer thereof.

8. The system of claim 4, wherein the polyalkene is polyethylene or a copolymer thereof.

9. The system of claim 1, wherein the container is substantially rigid such that the cavity defines a fixed volume.

10. The system of claim 1, wherein the first end comprises a threaded region extending around an outer surface of the container, wherein the system further comprises a lid having a threaded region configured to engage the first end threaded region, such that the engagement of the first end threaded region and the lid threaded region seals the first end.

11. The system of claim 10, further comprising a seal member configured to be disposed between and in contact with the lid threaded region and the first end threaded region.

12. The system of claim 1, wherein the container is substantially deformable and the cavity defines a first geometry having a first volume when the first end is open, and wherein the container is configured to deform upon application of pressure such that the cavity assumes a second geometry having a second volume smaller than the first volume.

13. The system of claim 1, wherein the first end is substantially deformable such that opposing walls of the inner surface at the first end are configured to contact one another upon application of force and seal the first end.

14. The system of claim 13, wherein at least a portion of the inner surface at the first end comprises an amount of sealing agent configured to bond the opposing walls to one another so as to seal the first end.

15. The system of claim 14, wherein the sealing agent comprises an adhesive material or a thermal bonding material.

16. The system of claim 13, further comprising a mechanical fastener configured to keep the opposing walls in contact with one another so as to seal the container.

17. The system of claim 1, wherein the second end defines a sealable opening extending into the cavity.

18. The system of claim 17, wherein the second end is substantially deformable such that opposing walls of the inner surface at the second end are configured to contact one another upon application of force and seal the second end.

* * * * *